US 012350281B2

(12) United States Patent
Dempsey et al.

(10) Patent No.: US 12,350,281 B2
(45) Date of Patent: Jul. 8, 2025

(54) LONG-ACTING INJECTABLE FORMULATIONS AND USE THEREOF

(71) Applicant: DECHRA VETERINARY PRODUCTS, LLC, Overland Park, KS (US)

(72) Inventors: Gail L. Dempsey, Greensboro, NC (US); Douglas L. Hepler, Greensboro, NC (US); Dorothea Erxleben, Greensboro, NC (US); Michael S. Daniel, Greensboro, NC (US); Neil E. Paulsen, Greensboro, NC (US)

(73) Assignee: Dechra Veterinary Products, LLC, Overland Park, KS (US)

( * ) Notice: Subject to any disclaimer, the term of this patent is extended or adjusted under 35 U.S.C. 154(b) by 378 days.

(21) Appl. No.: 16/879,626

(22) Filed: May 20, 2020

(65) Prior Publication Data

US 2020/0368263 A1    Nov. 26, 2020

Related U.S. Application Data

(60) Provisional application No. 62/852,527, filed on May 24, 2019.

(51) Int. Cl.
| | |
|---|---|
| *A61K 31/7048* | (2006.01) |
| *A61K 9/00* | (2006.01) |
| *A61K 31/137* | (2006.01) |
| *A61K 31/497* | (2006.01) |
| *A61K 31/573* | (2006.01) |
| *A61K 47/14* | (2017.01) |
| *A61K 47/26* | (2006.01) |
| *A61K 47/28* | (2006.01) |

(52) U.S. Cl.
CPC ........ *A61K 31/7048* (2013.01); *A61K 9/0019* (2013.01); *A61K 31/137* (2013.01); *A61K 31/497* (2013.01); *A61K 31/573* (2013.01); *A61K 47/14* (2013.01); *A61K 47/26* (2013.01); *A61K 47/28* (2013.01)

(58) Field of Classification Search
CPC ............. A61K 31/7048; A61K 31/137; A61K 31/573; A61K 9/0019; A61K 47/14; A61K 47/26; A61K 47/28
See application file for complete search history.

(56) References Cited

U.S. PATENT DOCUMENTS

| | | | |
|---|---|---|---|
| 6,552,002 B2 | 4/2003 | Steber et al. | |
| 9,956,164 B2 | 5/2018 | Zaremba et al. | |
| 2008/0085263 A1* | 4/2008 | Thuresson | A61K 8/68 514/315 |
| 2012/0058187 A1* | 3/2012 | Lallemand | A61K 31/573 424/133.1 |
| 2013/0156853 A1 | 6/2013 | Zhang et al. | |
| 2014/0275261 A1 | 9/2014 | Okumu et al. | |
| 2015/0290322 A1 | 10/2015 | Yoon et al. | |
| 2016/0000797 A1* | 1/2016 | Checcone | A61K 31/57 424/432 |
| 2018/0117016 A1 | 5/2018 | Tamraz et al. | |
| 2018/0256622 A1 | 9/2018 | Hepler et al. | |
| 2018/0344629 A1 | 12/2018 | Hepler et al. | |

FOREIGN PATENT DOCUMENTS

| | | | |
|---|---|---|---|
| CN | 1686156 | * | 10/2005 |
| CN | 1895262 A | | 1/2007 |
| CN | 102617595 | * | 8/2012 |
| CN | 109310680 A | | 2/2019 |
| CN | 2019048799 | * | 3/2019 |
| JP | S54-132223 A | | 10/1979 |
| JP | H11-507278 A | | 6/1999 |
| JP | 2001-261558 A | | 9/2001 |
| JP | 2001-524510 A | | 12/2001 |
| JP | 2003-508449 A | | 3/2003 |
| JP | 2003-525892 A | | 9/2003 |
| JP | 2005-537280 A | | 12/2005 |
| JP | 2009-519253 A | | 5/2009 |
| JP | 2013-536805 A | | 9/2013 |
| JP | 2016-504352 A | | 2/2016 |
| JP | 2017-506671 A | | 3/2017 |
| WO | WO2010129622 | * | 11/2010 |
| WO | WO 2013/057208 A1 | | 4/2013 |
| WO | WO2017023694 | * | 2/2017 |
| WO | WO 2018/005777 | * | 4/2018 |

OTHER PUBLICATIONS

Zhang, CN 1686156, puclished: Oct. 26, 2005, English machine translation obtained Sep. 26, 2022. (Year: 2022).*
Yoshida, CN 2019048799, published: Mar. 28, 2019, English machine translation obtained on May 29, 2023. (Year: 2023).*
Zejin et al. CN 102617595, published: Aug. 1, 2012; English machine translation obtained on Sep. 18, 2024. (Year: 2024).*
International Search Report issued on Aug. 17, 2020, regarding PCT/US2020/033839.
Extended European Search Report for EP 20815338.7 dated May 17, 2023, 13 pages.
Matschke et al., "Sustained-Release Injectables Formed In Situ And Their Potential Use For Veterinary Products," Journal of Controlled Release, vol. 85, pp. 1-15, 2002.
CN Office Action in Chinese Application No. 202080035528.6, dated Nov. 28, 2022, 15 pages (with English translation).
JP Office Action in Japanese Application No. 2021-569299, dated Jan. 23, 2024, 12 pages (with English translation).
JP Office Action in Japanese Application No. 2021-569299, dated Jul. 29, 2024, 8 pages (with English translation).

* cited by examiner

*Primary Examiner* — Genevieve S Alley
(74) *Attorney, Agent, or Firm* — DLA Piper LLP (US)

(57) ABSTRACT

Provided herein are long-acting, non-aqueous pharmaceutically acceptable compositions of active ingredients for subcutaneous injection.

17 Claims, 4 Drawing Sheets

LONG-ACTING INJECTABLE FORMULATIONS AND USE THEREOF

CROSS REFERENCE TO RELATED APPLICATION

This application claims the benefit of priority to U.S. Provisional Patent Application Ser. No. 62/852,527, filed on May 24, 2019. The entire contents of the foregoing is hereby incorporated by reference in its entirety.

BACKGROUND OF THE INVENTION

Field Of The Invention

The invention relates generally to long-acting, non-aqueous, subcutaneously injectable formulations and more specifically to long-acting formulations especially for use in mammals.

Background Information

Conventional long-acting injections consist either of lipophilic drugs in aqueous solvents as suspensions or of lipophilic drugs dissolved in vegetable oils. Poorly water-soluble salt formulations can be used to control the dissolution rate of drug particles to prolong the absorption. However, several other factors such as injection site, injection volume, the extent of spreading of the depot at the injection site, and the absorption and distribution of the oil vehicle per se might affect the overall pharmacokinetic profile of the drug.

Biodegradable microsphere systems are also available for use in extended release formulations, made with an appropriate biodegradable polymer. The release of the drug molecule from biodegradable microspheres is controlled by diffusion through the polymer matrix and polymer degradation. A variety of biodegradable polymers for controlled drug delivery intensively studied over the past several decades. See, Pandya et al., *International Journal of Biopharmaceutics* 5(3):208-213 (2014); see also Matschke et al., *Journal of Controlled Release* 85 (1-3):1-15 (2002).

The manufacturing of such conventional extended release formulations is complex and costly requiring, as noted, added heat, evaporation steps, application of added pressure (e.g., through compression or extrusion) and/or use of significant quantities of organic solvents which could introduce potential toxicity if not completely removed. It is also difficult to appropriately control the release of a drug that is in an injectable dosage form in order to achieve the desired onset and duration of therapeutic effects in a target species. Therefore, it would be desirable to have compositions and less complex methods of providing prolonged therapeutic relief to a mammal while minimizing the number of administrations/doses that must be given to the mammal.

SUMMARY OF THE INVENTION

Provided herein is a long-acting, non-aqueous injectable pharmaceutically acceptable composition.

In one embodiments, the injectable pharmaceutically acceptable composition includes:
 a) a pharmaceutically active agent;
 b) a polar lipid, such as glycerol monooleate and/or glycerol monostearate, at about 5.0 to 40.0% w/w; and
 c) a triglyceride carrier at about 5.0 to 70.0% w/w.

Optionally, the composition further includes an excipient, such as an alcohol (e.g., ethanol and/or benzyl alcohol), which may be present at up to about 10.0 to 20.0% w/w, including 10.0, 11.0, 12.0, 13.0, 14.0, 15.0, 16.0, 17.0, 18.0, 19.0 or 20.0% w/w.

Optionally, the composition further includes sucrose acetate isobutyrate (SAIB) which may be present at up to about 5.0 to 50.0 or 70.0% w/w.

In another embodiment, the injectable pharmaceutically acceptable composition includes:
 a) a pharmaceutically active agent;
 b) SAIB at about 5.0 to 70.0% w/w; and
 c) a water miscible solvent, such as triacetin, at about 30.0 to 70.0% w/w.

Optionally, the composition further includes an excipient, such as an alcohol (e.g., ethanol and/or benzyl alcohol), which may be present at up to about 10.0 to 20.0% w/w, including 10.0, 11.0, 12.0, 13.0, 14.0, 15.0, 16.0, 17.0, 18.0, 19.0 or 20.0% w/w.

In another embodiment, the injectable pharmaceutically acceptable composition includes:
 a) a pharmaceutically active agent;
 b) sucrose acetate isobutyrate at about 5.0 to 70.0% w/w; and
 c) a triglyceride carrier at about 5.0 to 70.0% w/w.

Optionally, the composition further includes a water miscible solvent, such as triacetin, at about 30.0 to 70.0% w/w.

Optionally, the composition further includes an excipient, such as an alcohol (e.g., ethanol and/or benzyl alcohol), which may be present at up to about 10.0 to 20.0% w/w, including 10.0, 11.0, 12.0, 13.0, 14.0, 15.0, 16.0, 17.0, 18.0, 19.0 or 20.0% w/w.

In various embodiments, an alcohol for use in the pharmaceutically acceptable composition of the invention includes one or more alcohols and/or glycols. Such alcohols are pharmaceutically acceptable and are generally liquids at about room temperature, approximately 20° C. By way of illustration, an alcohol or glycol for use in the composition of the invention may include one or more of propylene glycol, ethanol, 2-(2-ethoxyethoxy)ethanol (Transcutol®), benzyl alcohol, glycerol, polyethylene glycol 200, polyethylene glycol 300, polyethylene glycol 400 and the like.

In various embodiments, the pharmaceutically acceptable composition is a sterile injectable liquid that once injected subcutaneously increases in viscosity thereby forming an in-situ forming depot (ISFD) which provides sustained release of the pharmaceutically active agent. The ISFD is formed by a depot forming agent that precipitates and entraps the pharmaceutically active agent upon subcutaneous injection. This precipitate yields a semi-solid, water insoluble depot that biodegrades and/or allows diffusion of the pharmaceutically active agent over an extended time period. Remarkably, the composition of the present invention provides at least up to about 48, 60, 72, 84, 96, 108, 120, 132, 144, 156, 168 hours or greater of active release of the pharmaceutically active agent when administered by injection, such as subcutaneous or intramuscular injection, to a mammal.

In certain aspects, an exemplary formulation is as set forth in Table I below, where marbofloxacin may be substituted with any pharmaceutically active agent.

TABLE I

| Formulation | |
|---|---|
| Component | w/w % |
| Marbofloxacin | 20 |
| Medium chain triglycerides | 37 |
| Benzyl Alcohol | 10 |
| Ethanol | 5 |
| Glycerol monooleate | 16 |
| Polyoxyl castor oil | 8 |
| Hydrogenated phosphatidylcholine from soybean lecithin | 4 |
| | 100 |

In certain aspects, an exemplary formulation is as set forth in Table II below, where marbofloxacin may be substituted with any pharmaceutically active agent.

TABLE II

| Formulation | |
|---|---|
| Component | w/w % |
| Marbofloxacin | 10 |
| Medium chain triglycerides | 35 |
| Benzyl Alcohol | 5 |
| Glycerol monooleate | 20 |
| SAIB | 30 |
| | 100 |

In certain aspects, an exemplary formulation is as set forth in Table III below, where marbofloxacin may be substituted with any pharmaceutically active agent.

TABLE III

| Formulation | |
|---|---|
| Component | w/w % |
| Marbofloxacin | 20 |
| Medium chain triglycerides | 50 |
| Benzyl Alcohol | 5 |
| Ethanol | 5 |
| Glycerol monooleate | 20 |
| | 100 |

In certain related aspects, an exemplary formulation is as set forth in Table IV below, where marbofloxacin may be substituted with any pharmaceutically active agent.

TABLE IV

| Formulation | |
|---|---|
| Component | w/w % |
| Marbofloxacin | 20 |
| Medium chain triglycerides | 36-37 |
| Benzyl Alcohol | 10 |
| Ethanol | 5 |
| Glycerol monooleate | 20 |

TABLE IV-continued

| Formulation | |
|---|---|
| Component | w/w % |
| Polyoxyl castor oil | 3 |
| Hydrogenated phosphatidylcholine from soybean lecithin | 5 |
| Vitamin E | 0.01-0.1 |
| | 100 |

In certain related aspects, an exemplary formulation is as set forth in Table V below, where terbinafine may be substituted with any pharmaceutically active agent.

TABLE V

| Formulation | |
|---|---|
| Component | w/w % |
| Terbinafine | 14-16 |
| Triacetin | 42-47 |
| SAIB | 35-40 |
| Ethanol | 2-6 |
| | 100 |

In certain related aspects, an exemplary formulation is as set forth in Table VI below, where florfenicol may be substituted with any pharmaceutically active agent.

TABLE VI

| Formulation | |
|---|---|
| Component | w/w % |
| Florfenicol | 15 |
| Triacetin | 44 |
| SAIB | 37 |
| Ethanol | 4 |
| | 100 |

In certain related aspects, an exemplary formulation is as set forth in Table VII below, where florfenicol may be substituted with any pharmaceutically active agent.

TABLE VII

| Formulation | |
|---|---|
| Component | w/w % |
| Florfenicol | 20 |
| Glycerol monooleate | 20 |
| Benzyl alcohol | 4 |
| Ethanol | 5 |
| Polyoxyl castor oil | 3 |
| Medium chain triglycerides | 47 |
| | 100 |

In certain aspects, the pharmaceutically active agent is present in an amount of about 0.25 to 25.0% w/w. In other aspects, the triglycerides are caprylic/capric triglycerides or caprylic triglycerides. In other embodiments, the triglyceride is present in an amount of up to about 70.0% w/w ±10.0% w/w. In some aspects, the composition further comprises benzyl alcohol and/or ethanol and optionally cholesterol, such as milled cholesterol, each being present in an amount of about 1.0 to 20.0% w/w, about 1.0 to 20.0% w/w and about 1.0 to 2.0 or 3.0% w/w of the formulation respectively. In other aspects, the composition is sterile and formulated for administration by injection.

Also provided herein is a method of treating a disease or disorder (e.g., infection, inflammatory disorder or pain) in a subject by administering a formulation of the invention. Surprisingly, a clinically effective amount of the pharmaceutically active agent when provided in a formulation of the invention is present in the blood stream of the subject for about 48, 60, 72, 84, 96, 108, 120, 132, 144, 156, 168 hours or greater after administration. In various embodiments, a single, or multiple pharmaceutically active agents are administered in a single formulation. In an embodiment, a formulation of the invention including marbofloxacin, terbinafine, tulathromycin, all optionally combined with buprenorphine or morphine, is delivered to a companion animal such as a cat or dog.

In certain aspects, formulations including marbofloxacin and/or tulathromycin are particularly suited for treatment of canines for an infection, such as urinary tract infection or other microbial infection.

In certain aspects, formulations including terbinafine are particularly suited for treatment of felines for an infection, such as ringworm or other microbial infection.

DETAILED DESCRIPTION OF THE INVENTION

Figure 1:
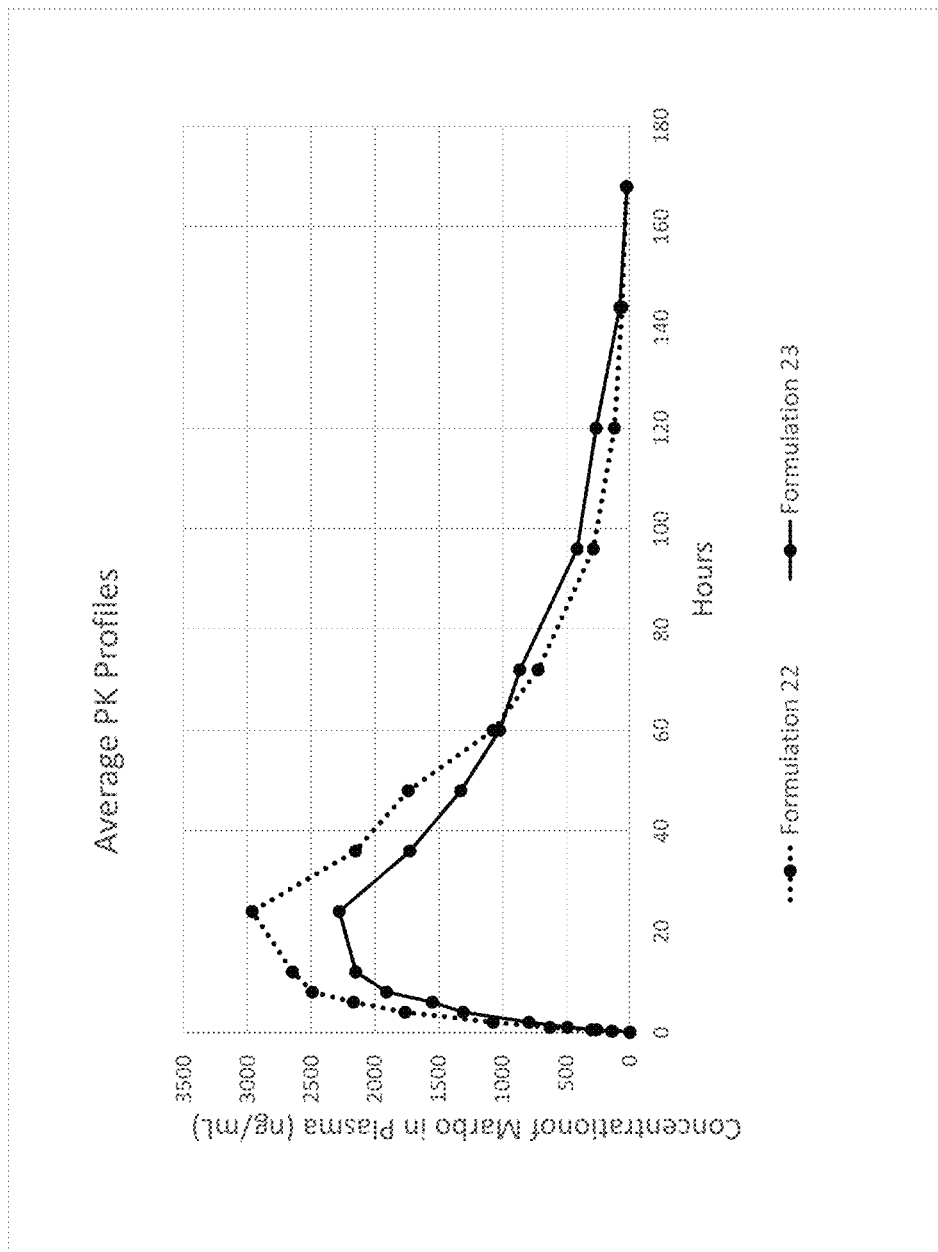
FIG. 1 is a graphical representation depicting data in one embodiment of the invention.

The following terms, definitions and abbreviations apply. Abbreviations used herein have their conventional meaning within the chemical and biological arts.

The term "subject" refers to mammalian organisms to be treated by the methods of the disclosure. Such organisms include, but are not limited to, companion animals such as domestic dogs and cats. In the context of the disclosure, the term "subject" generally refers to an individual who will receive or who has received treatment described below (e.g., administration of the compositions of the disclosure).

As used herein, a "patient" or "subject" refers to either a human or non-human mammalian animal. Non-human animals include any non-human mammalian animals. Such non-human animals may include, but are not limited to rodents, non-human primates (e.g., monkey and apes), ungulates, ovines, bovines, ruminants, lagomorphs, porcines, caprines, equines, canines, felines, murines, and the like. In certain embodiments of the invention, the animals are mammals. In some embodiments, the animals include, but are not limited to, companion animals such as domestic dogs and cats. In the context of the disclosure, the term "subject" generally refers to an individual who will receive or who has received treatment described below (e.g., administration of a composition of the disclosure).

The term "therapeutically effective amount" means the amount of the compound or pharmaceutical composition that will elicit the biological or medical response of a patient or tissue that is being sought by the researcher, veterinarian, medical doctor or other clinician.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the disclosure or pharmaceutical composition to the subject in need of treatment.

The term "about" with respect to a number means that the number includes a range of insignificant variation above and below the number unless otherwise stated; e.g., a value of 1 will be understood to include up to 0.5 to 1.5 and all numbers thereinbetween.

In embodiments, the pharmaceutical compositions of the invention are in the form of a sterile injectable liquid of an active such as marbofloxacin, florfenicol, terbinafine, tulathromycin and/or buprenorphine, or other pharmaceutically active agent such as those disclosed below, in a carrier including (i) a polar lipid, (ii) a medium chain triglyceride carrier, such as a caprylic/capric triglyceride, and (iii) optionally SAIB.

In embodiments, the pharmaceutical compositions of the invention are in the form of a sterile injectable liquid of an active such as marbofloxacin, florfenicol, terbinafine, tulathromycin and/or buprenorphine, or other pharmaceutically active agent such as those disclosed below, in a carrier including (i) SAIB, (ii) a medium chain triglyceride carrier, such as a caprylic/capric triglyceride, and (iii) optionally a polar lipid.

In one embodiment, the polar lipid is glycerol monooleate, glycerol monostearate, or a combination thereof.

In certain aspects, the polar lipid is glycerol monooleate, glycerol monostearate, glycerol monolinoleate, glycerol monocaprylate, glycerol monocaprate, glycerol monolaurate, glycerol monomyristic, glycerol monopalmitic, glycerol monomyristoleic, glycerol monopalmitoleic, glycerol monosapienic or any combination thereof.

In certain aspects, the polar lipid is glycerol monooleate, glycerol monostearate, or a combination thereof.

In certain aspects, the polar lipid is phosphatidylcholine, phosphatidylethanolamine, phosphatidylserine, phosphatidylinositol, glycerophosphocholine, phosphatidic acid, a phospholipid from egg, soybean, rapeseed, canola, or sunflower oil, a synthetic or naturally occurring phospholipid, a hydrogenated or non-saturated phospholipid, a PEGylated phospholipid or any combination thereof.

In another embodiment, the pharmaceutical compositions of the invention are in the form of a sterile injectable liquid of an active such as marbofloxacin, florfenicol, terbinafine, tulathromycin and/or buprenorphine, or other pharmaceutically active agent such as those disclosed below, in a carrier including (i) SAIB, and (ii) a water miscible solvent. In one embodiment, the water miscible solvent is triacetin.

In certain aspects, the water miscible solvent is a triglyceride, triethyl, triester or combination thereof. In embodiments, the water miscible solvent is triacetin, triethyl citrate, or combination thereof.

When present, the triglyceride is present in an amount of about 5.0 to 70.0% w/w, or 10.0 to 60.0% w/w or 30.0 to 55.0% w/w. In some embodiments, the triglyceride is caproic acid, caprylic acid, capric acid, lauric acid, myristic acid or any combination thereof. For example, the triglyceride is a medium chain triglyceride, such as caprylic/capric (C8 and/or C10) triglycerides or caprylic (C8) triglycerides. In embodiments, the triglyceride is a mixture of caprylic acid and capric acid wherein the mixture comprises about 40.0 to 85.0% caprylic acid and about 15.0 to 60.0% capric acid, or wherein the mixture comprises about 50.0 to 80.0% caprylic acid and about 20.0 to 50.0% capric acid, or wherein the mixture comprises about 65.0 to 80.0% caprylic acid and about 20.0 to 35.0% capric acid, or wherein the mixture comprises about 50.0 to 65.0% caprylic acid and about 30.0 to 45.0% capric acid. In one embodiment, the triglyceride may be a fatty acid ester emollient, such as a saturated coconut and palm kernel oil-derived caprylic/capric fatty acid mixture with glycerin in a solid form sold under the trademark MIGLYOL™. In another embodiment, the triglyceride may be a fatty acid ester emollient, such as a saturated coconut and palm kernel oil-derived caprylic/capric fatty acid mixture sold under the trademark CAPTEX™, such as CAPTEX™ 8000.

It will be appreciated that the triglyceride used in the composition may be entirely substituted or supplement with a monoglyceride or diglyceride, the fatty acid moieties of which are saturated or unsaturated, preferably saturated, and contain from 6 to 30 carbon atoms. In some embodiments, the fatty acid moieties of the glyceride contain from 18 to 24 carbon atoms, more preferably from 20 to 22 carbon atoms.

The term 'saturated' as used herein refers to fatty acid moieties containing only carbon-carbon single bonds, e.g., an alkyl group. The term 'unsaturated' as used herein refers to fatty acid moieties containing at least one carbon-carbon double or triple bond (e.g., an alkenyl group, —CH$_2$=CH$_2$—, or an alkynyl group, —CH≡CH—). Any alkenyl groups which may be present may exist in either cis or trans geometries. In some embodiments, the fatty acid moieties of the fat are either saturated, or unsaturated with one or more alkenyl groups.

The composition may also contain a polar lipid, such as glycerol monooleate and/or glycerol monostearate, in an amount of about 5.0 to 40.0% w/w of the composition, or 10.0 to 40.0% w/w, or 15.0 to 30.0% w/w or 17.0 to 25.0% w/w or 19.0 to 21.0% w/w, such as about 20.0% w/w.

The composition may also contain SAM in an amount of about 5.0 to 70.0% w/w of the composition, or 5.0 to 65.0% w/w, or 10.0 to 55.0% w/w or 10.0 to 45.0% w/w or 15.0 to 40.0% w/w, such as about 35.0 to 40.0% w/w.

The composition may also contain a water miscible solvent, such as a triglyceride (e.g., triacetin), triethyl and/or triester, in an amount of about 30.0 to 60.0% w/w of the composition, or 30.0 to 55.0% w/w, or 35.0 to 50.0% w/w or 35.0 to 45.0% w/w or 37.0 to 45.0% w/w, such as about 40.0 to 45.0% w/w.

The composition may also contain cholesterol particles, such as milled cholesterol, in an amount of about 1.0 to 10.0% w/w of the composition, or 1.0 to 7.0% w/w, or 1.0 to 5.0% w/w or 1.0 to 4.0% w/w or 2.0 to 4.0% w/w, such as about 3.0% w/w.

The composition may also contain excipients. In certain aspects, the excipient is ethanol or benzyl alcohol. In certain such embodiments, the excipient is present in an amount of about 1 to 20%, 5 to 20% or 10 to 20% w/w, for example about 10, 11, 12, 13, 14, 15, 16, 17, 18, 19 or 20% w/w. Other suitable excipients include ethanol, 2-ethoxy (2-ethoxy) ethanol, ethyl oleate, ethyl acetate, ethyl benzoate, benzyl alcohol, glycerol, polyethylene glycol 200, polyethylene glycol 300, polyethylene glycol 400, benzyl benzoate, isopropyl myristate, isopropyl alcohol, 2-pyrrolidone, DMSO, polyvinylpyrrolidone (e.g., PVP K17), propylene carbonate, glycofurol, N-methylpyrrolidone, propylene glycol, acetone, methyl acetate, methyl ethyl ketone, dimethylformamide, dimethylsulfoxide, tetrahydrofuran, caprolactam, decylmethylsulfoxide, tetrahydrofuran, caprolactam, decylmethylsulfoxide, and oleic acid, 1-dodecylazacycloheptan-2-one. In certain embodiments, benzyl alcohol and/or ethanol is present in an amount of about 1 to 25%, 1 to 20%, 5 to 20%, 5 to 15%, such as about 5 to 15% w/w. In embodiments, benzyl alcohol is present in an amount of about 5 to 20%, 10 to 20%, 10 to 15%, or 15 to 20 w/w; and ethanol is present in an amount of about 1 to 10%, 2 to 10%, 3 to 8%, 4 to 7%, or about 1, 2, 3, 4, 5, 6, 7, 8, 9 or 10% w/w.

Also, while the pharmaceutically active agent may be in its hydrated form, no water is added to the composition during or after mixture. As such, the composition described herein is substantially non-aqueous, for example, the composition has less than about 3.0, 2.5, 2.0, 1.5, 1.0, 0.9, 0.8, 0.7, 0.6, 0.5, 0.4, 0.3, 0.2, 0.1, 0.5 or 0.1% w/w of an aqueous substance, such as water.

Any or all of the components of the composition may be included in their dehydrated form or their anhydrous form.

An exemplary formulation is as set forth in Table VIII below, where marbofloxacin may be substituted with any pharmaceutically active agent.

TABLE VIII

| Formulation | |
|---|---|
| Component | w/w % |
| Marbofloxacin | 15-25 |
| Medium chain triglycerides (e.g., caprickaprylic triglycerides) | 30-40 |
| Benzyl Alcohol | 5-15 |
| Ethanol | 1-10 |
| Glycerol monooleate | 10-40 |
| Polyoxyl castor oil | 5-10 |
| Hydrogenated phosphatidylcholine from soybean lecithin | 2-6 |
| | 100 |

An exemplary formulation is as set forth in Table IX below, where marbofloxacin may be substituted with any pharmaceutically active agent.

TABLE IX

| Formulation | |
|---|---|
| Component | w/w % |
| Marbofloxacin | 10-20 |
| Medium chain triglycerides (e.g., caprickaprylic triglycerides) | 30-40 |
| Benzyl Alcohol | 1-10 |
| Glycerol monooleate | 15-40 |
| SAIB | 25-70 |
| | 100 |

An exemplary formulation is as set forth in Table X below, where marbofloxacin may be substituted with any pharmaceutically active agent.

TABLE X

| Formulation | |
|---|---|
| Component | w/w % |
| Marbofloxacin | 15-25 |
| Medium chain triglycerides (e.g., caprickaprylic triglycerides) | 40-55 |
| Benzyl Alcohol | 0-10 |
| Ethanol | 0-10 |
| Glycerol monooleate | 15-40 |
| | 100 |

An exemplary formulation is as set forth in Table XI below, where marbofloxacin may be substituted with any pharmaceutically active agent.

TABLE XI

| Formulation | |
|---|---|
| Component | w/w % |
| Marbofloxacin | 15-25 |
| Medium chain triglycerides (e.g., caprickaprylic triglycerides) | 30-40 |
| Benzyl Alcohol | 5-15 |
| Ethanol | 0-10 |
| Glycerol monooleate | 15-40 |
| Polyoxyl castor oil | 1-5 |
| Hydrogenated phosphatidylcholine from soybean lecithin | 1-10 |
| Vitamin E | 0.01-0.1 |
| | 100 |

An exemplary formulation is as set forth in Table XII below, where terbinafine may be substituted with any pharmaceutically active agent.

TABLE XII

| Formulation | |
|---|---|
| Component | w/w % |
| Terbinafine | 15-20 |
| Triacetin | 40-45 |
| SAIB | 35-70 |
| Ethanol | 1-10 |
| | 100 |

Other exemplary formulation according to embodiments of the invention are set forth in Table XIII, where the pharmaceutically active agent may be substituted with any active.

TABLE XIII

| Formulations | |
|---|---|
| Identifier | Formula (w/w %) |
| 1 | 20% Marbofloxacin<br>60% C8 triglyceride<br>12% Glycerol monooleate<br>3% Hydrogenated phosphatidylcholine from soybean lecithin<br>5% hydroxypropyl methylcellulose (HPMC), 4k cps |
| 2 | 15% Glycerol monooleate<br>10% Ethanol<br>55% C8 triglyceride<br>20% Marbofloxacin |
| 3 | 15% Glycerol monooleate<br>10% 2-Pyrrolidone<br>55% C8 triglyceride<br>20% Marbofloxacin |
| 4 | 10% Ethanol<br>15% Glycerol monooleate<br>50% C8 triglyceride<br>5% HPMC (100 cps)<br>20% Marbofloxacin |
| 5 | 20% Marbofloxacin<br>12% Glycerol monooleate<br>6% Polyoxyl castor oil<br>3% Hydrogenated phosphatidylcholine from soybean lecithin<br>10% Benzyl Alcohol<br>49% C8 triglyceride |
| 6 | 20% Marbofloxacin<br>12% Glycerol monooleate<br>3% Hydrogenated phosphatidylcholine from soybean lecithin<br>6% Polyoxyl castor oil<br>2% Benzyl Alcohol<br>57% C8 triglyceride |
| 7 | 20% Marbofloxacin<br>17% Glycerol monooleate<br>3% Hydrogenated phosphatidylcholine from soybean lecithin<br>6% Polyoxyl castor oil<br>10% Benzyl Alcohol<br>44% C8 triglyceride |
| 8 | 5% Ethanol<br>5% Benzyl Alcohol<br>52% C8 triglyceride<br>3% Cholesterol<br>15% Glycerol monooleate<br>20% Marbofloxacin |
| 9 | 20% Marbofloxacin<br>16% Glycerol monooleate<br>4% Hydrogenated phosphatidylcholine from soybean lecithin<br>6% Polyoxyl castor oil<br>10% Benzyl Alcohol<br>44% C8 triglyceride |
| 10 | 20% Marbofloxacin<br>16% Glycerol monooleate<br>4% Hydrogenated phosphatidylcholine from soybean lecithin<br>10% Benzyl Alcohol<br>50% C8 triglyceride |
| 11 | 20% Marbofloxacin<br>16% Glycerol monooleate<br>4% Hydrogenated phosphatidylcholine from soybean lecithin<br>10% Benzyl Alcohol<br>5% Ethanol<br>50% C8 triglyceride |
| 12 | 5% Ethanol<br>5% Benzyl Alcohol<br>5% Hydrogenated phosphatidylcholine from soybean lecithin<br>45% C8 triglyceride<br>20% Glycerol monooleate<br>20% Marbofloxacin |
| 13 | 5% Ethanol<br>5% Benzyl Alcohol<br>50% C8 triglyceride<br>20% Glycerol monooleate<br>20% Marbofloxacin |
| 14 | 20% Marbofloxacin<br>12% Glycerol monooleate |

TABLE XIII-continued

Formulations

| Identifier | Formula (w/w %) |
|---|---|
|  | 6% Polyoxyl castor oil |
|  | 3% Hydrogenated phosphatidylcholine from soybean lecithin |
|  | 10% Benzyl Alcohol |
|  | 5% Ethanol |
|  | 44% C8 triglyceride |
| 15 | 20% Marbofloxacin |
|  | 12% Glycerol monooleate |
|  | 3% Polyoxyl castor oil |
|  | 3% Hydrogenated phosphatidylcholine from soybean lecithin |
|  | 10% Benzyl Alcohol |
|  | 5% Ethanol |
|  | 47% C8 triglyceride |
| 16 | 20% Marbofloxacin |
|  | 16% Glycerol monooleate |
|  | 8% Polyoxyl castor oil |
|  | 4% Hydrogenated phosphatidylcholine from soybean lecithin |
|  | 10% Benzyl Alcohol |
|  | 5% Ethanol |
|  | 37% C8 triglyceride |
| 17 | 20% Marbofloxacin |
|  | 20% Glycerol monooleate |
|  | 10% Polyoxyl castor oil |
|  | 5% Hydrogenated phosphatidylcholine from soybean lecithin |
|  | 10% Benzyl Alcohol |
|  | 5% Ethanol |
|  | 30% C8 triglyceride |
| 18 | 5% Ethanol |
|  | 5% Benzyl Alcohol |
|  | 47% C8 triglyceride |
|  | 3% Cholesterol |
|  | 20% Glycerol monooleate |
|  | 20% Marbofloxacin |
| 19 | 5% Ethanol |
|  | 5% Benzyl Alcohol |
|  | 39% C8 triglyceride |
|  | 6% Polyoxyl castor oil |
|  | 5% Hydrogenated phosphatidylcholine from soybean lecithin |
|  | 20% Glycerol monooleate |
|  | 20% Marbofloxacin |
| 20 | 20% Marbofloxacin |
|  | 20% Glycerol monooleate |
|  | 10% Polyoxyl castor oil |
|  | 5% Hydrogenated phosphatidylcholine from soybean lecithin |
|  | 10% Benzyl Alcohol |
|  | 5% Ethanol |
|  | 0.07% Vitamin E |
|  | 29.93% C8 triglyceride |
| 21 | 20% Marbofloxacin |
|  | 20% Glycerol monooleate |
|  | 5% Polyoxyl castor oil |
|  | 5% Hydrogenated phosphatidylcholine from soybean lecithin |
|  | 10% Benzyl Alcohol |
|  | 5% Ethanol |
|  | 0.07% Vitamin E |
|  | 34.93% C8 triglyceride |
| 22 | 5% Dehydrated Ethanol |
|  | 5% Benzyl Alcohol |
|  | 50% C8/C10 triglyceride |
|  | 20% Glycerol monooleate |
|  | 20% Marbofloxacin |
| 23 | 20% Marbofloxacin |
|  | 20% Glycerol monooleate |
|  | 3% Polyoxyl castor oil |
|  | 5% Hydrogenated phosphatidylcholine from soybean lecithin |
|  | 10% Benzyl Alcohol |
|  | 5% Dehydrated Ethanol |
|  | 0.07% Vitamin E |
|  | 36.93% C8/C10 triglyceride |
| 24 | 10% Marbofloxacin |
|  | 30% SAIB |
|  | 20% Glycerol monooleate |
|  | 5% Benzyl Alcohol |
|  | 35% C8/C10 triglyceride |
| 25 | 20% Marbofloxacin |
|  | 36.99% SAIB |
|  | 4.11% Ethanol |
|  | 38.89% Triacetin |
| 26 | 10% Marbofloxacin |
|  | 20% Glycerol monooleate |
|  | 5% Benzyl Alcohol |
|  | 5% SAIB |
|  | 60% C8/C10 triglyceride |
| 27 | 20% Marbofloxacin |
|  | 20% Glycerol monooleate |
|  | 5% Benzyl Alcohol |
|  | 5% SAIB |
|  | 50% C8/C10 triglyceride |
| 28 | 20% Marbofloxacin |
|  | 5% Benzyl Alcohol |
|  | 55% C8/C10 triglyceride |
|  | 20% Glycerol monooleate |
| 29 | 5% Dehydrated Ethanol |
|  | 5% Benzyl Alcohol |
|  | 45% C8/C10 triglyceride |
|  | 20% Glycerol monooleate |
|  | 20% Marbofloxacin |
|  | 5% SAIB |
| 30 | 5% Dehydrated Ethanol |
|  | 10% Benzyl Alcohol |
|  | 45% C8/C10 triglyceride |
|  | 20% Glycerol monooleate |
|  | 20% Marbofloxacin |
| 31 | 5% Dehydrated Ethanol |
|  | 5% Benzyl Alcohol |
|  | 55% C8/C10 triglyceride |
|  | 20% Glycerol monooleate |
|  | 15% Marbofloxacin |
| 32 | 5% Dehydrated Ethanol |
|  | 5% Benzyl Alcohol |
|  | 60% C8/C10 triglyceride |
|  | 20% Glycerol monooleate |
|  | 10% Marbofloxacin |
| 33 | 5% Dehydrated Ethanol |
|  | 10% Benzyl Alcohol |
|  | 40% C8/C10 triglyceride |
|  | 20% Glycerol monooleate |
|  | 20% Marbofloxacin |
|  | 5% SAIB |
| 34 | 5% Dehydrated Ethanol |
|  | 10% Benzyl Alcohol |
|  | 45% C8/C10 triglyceride |
|  | 20% Glycerol monooleate |
|  | 15% Marbofloxacin |
|  | 5% SAIB |
| 35 | 20% Marbofloxacin |
|  | 5% Dehydrated Alcohol |
|  | 5% Benzyl Alcohol |
|  | 20% Glycerol monooleate |
|  | 50% C8 triglyceride |
| 36 | 15% Marbofloxacin |
|  | 5% Dehydrated Alcohol |
|  | 5% Benzyl Alcohol |
|  | 20% Glycerol monooleate |
|  | 55% C8 triglyceride |
| 37 | 5% Dehydrated Ethanol |
|  | 5% Benzyl Alcohol |
|  | 47% Medium chain triglycerides (e.g., capric/caprylic triglycerides) |
|  | 20% Glycerol monooleate |
|  | 20% Marbofloxacin |
|  | 3% Polyoxyl castor oil |
| 38 | 5% Dehydrated Ethanol |
|  | 5% Benzyl Alcohol |
|  | 47% Medium chain triglycerides (e.g., |

TABLE XIII-continued

Formulations

| Identifier | Formula (w/w %) |
|---|---|
|  | capric/caprylic triglycerides)<br>20% Glycerol monooleate<br>20% Marbofloxacin |
| 39 | 3% Polyoxyl 15 hydroxystearate<br>5% Dehydrated Alcohol<br>5% Benzyl Alcohol<br>15% Glycerol monooleate<br>15% Marbofloxacin<br>60% Medium chain triglycerides (e.g., capric/caprylic triglycerides) |
| 40 | 5% Dehydrated Ethanol<br>55% Medium chain triglycerides (e.g., caprickaprylic triglycerides)<br>20% Glycerol monooleate<br>20% Marbofloxacin |
| 41 | 5% Dehydrated Ethanol<br>52% Medium chain triglycerides (e.g., caprickaprylic triglycerides)<br>20% Glycerol monooleate<br>20% Marbofloxacin<br>3% Polyoxyl castor oil |

Other exemplary formulation according to embodiments of the invention are set forth in Table XIV, where the pharmaceutically active agent may be substituted with any active.

TABLE XIV

Formulations

| Identifier | Formula (w/w %) |
|---|---|
| 42 | 15% Terbinafine HCl<br>41% SAIB<br>10% Ethanol<br>44% Triacetin |
| 43 | 15% Terbinafine HCl<br>5% Ethanol<br>5% Benzyl Alcohol<br>20% Glycerol monooleate<br>3% Cholesterol<br>52% C8 triglyceride |
| 44 | 15% Terbinafine HCl<br>5% Dehydrated Ethanol<br>5% Benzyl Alcohol<br>20% Glycerol monooleate<br>55% C8/C10 |
| 45 | 15% Terbinafine HCl<br>5% Ethanol<br>5% Benzyl Alcohol<br>20% Glycerol monooleate<br>55% C8/C10 Triglyceride |
| 46 | A:<br>40% SAIB<br>45% Triacetin<br>15% Terbinafine HCl<br>or<br>B:<br>40% SAIB<br>10% Benzyl Alcohol<br>35% Triacetin<br>15% Terbinafine HCl |
| 47 | 16.876% Terbinafine HCl<br>37% SAIB<br>4% Dehydrated Ethanol<br>42.124% Triacetin |
| 48 | 16.876% Terbinafine HCl<br>37% SAIB<br>46.124% C8/C10 triglyceride |
| 49 | 16.876% Terbinafine HCl<br>37% SAIB<br>5% Benzyl Alcohol<br>41.124% C8/C10 triglyceride |

TABLE XIV-continued

Formulations

| Identifier | Formula (w/w %) |
|---|---|
| 50 | 16.876% Terbinafine<br>37% SAIB<br>4% Benzyl Alcohol<br>42.124% Triacetin |

Other exemplary formulation according to embodiments of the invention are set forth in Table XV, where the pharmaceutically active agent may be substituted with any active.

TABLE XV

Formulations

| Identifier | Formula (w/w %) |
|---|---|
| 51 | 20% Tulathromycin<br>5% Ethanol, dehydrated 5% Benzyl alcohol<br>20% Glycerol monooleate<br>50% C8/C10 triglyceride |
| 52 | 15% Tulathromycin<br>30% Triacetin<br>20% Glycerol monooleate<br>10% Benzyl alcohol<br>10% C8/C10 triglyceride<br>10% SAIB<br>5% Ethanol, dehydrated |
| 53 | 15% Tulathromycin<br>25% Triacetin<br>20% Glycerol monooleate<br>10% benzyl alcohol<br>10% C8/C10 triglyceride<br>20% SAIB |
| 54 | 15% Tulathromycin<br>25% Triacetin<br>20% Glycerol monooleate<br>10% Benzyl alcohol<br>10% C8/C10 triglyceride<br>15% SAIB<br>5% Ethanol, dehydrated |
| 55 | 15% Tulathromycin<br>20% Glycerol monooleate<br>10% Benzyl alcohol<br>35% C8/C10 triglyceride<br>15% SAIB<br>5% Ethanol, dehydrated |
| 56 | 15% Tulathromycin<br>45% SAIB<br>25% C8/C10 triglyceride<br>10% Benzyl Alcohol<br>5% ethanol, dehydrated |
| 57 | 15% Tulathromycin<br>45% SAIB<br>25% 2-pyrrolidone<br>10% Benzyl Alcohol<br>5% Ethanol, dehydrated |
| 58 | 15% Tulathromycin<br>45% SAIB<br>25% Isopropyl myristate<br>10% Benzyl Alcohol<br>5% Ethanol, dehydrated |

Another exemplary formulation is as set forth in Table XVI below, where florfenicol may be substituted with any pharmaceutically active agent.

TABLE XVI

Formulation

| Component | w/w % |
|---|---|
| Florfenicol | 15-25 |
| Medium chain triglycerides (e.g., caprickaprylic triglycerides) | 40-60 |
| Benzyl Alcohol | 5-15 |
| Ethanol | 5-15 |
| Glycerol monooleate | 10-30 |
| Polyoxyl castor oil | 0-10 |
| | 100 |

Another exemplary formulation is as set forth in Table XVII below, where florfenicol may be substituted with any pharmaceutically active agent.

TABLE XVII

Formulation

| Component | w/w % |
|---|---|
| Florfenicol | 15-25 |
| Medium chain triglycerides (e.g., caprickaprylic triglycerides) | 45-50 |
| Benzyl Alcohol | 1-10 |
| Ethanol | 1-10 |
| Glycerol monooleate | 15-25 |
| Polyoxyl castor oil | 1-5 |
| | 100 |

An exemplary formulation is as set forth in Table XVIII below, where terbinafine may be substituted with any pharmaceutically active agent.

TABLE XVIII

Formulation

| Component | w/w % |
|---|---|
| Florfenicol | 10-20 |
| Triacetin | 40-50 |
| SAIB | 35-40 |
| Ethanol | 1-10 |
| | 100 |

Other exemplary formulation according to embodiments of the invention are set forth in Table XIX, where the pharmaceutically active agent may be substituted with any active.

TABLE XIX

Formulations

| Identifier | Formula (w/w %) |
|---|---|
| 59 | 15% Florfenicol<br>4% Ethanol, dehydrated<br>44% Triacetin<br>37% SAIB |
| 60 | 20% Florfenicol<br>20% Glycerol monooleate<br>5% Benzyl alcohol<br>47% C8/C10 triglyceride<br>3% Polyoxyl castor oil<br>5% Ethanol, dehydrated |

In certain related aspects, an exemplary formulation is as set forth in Table XX below, where terbinafine may be substituted with any pharmaceutically active agent.

TABLE XX

Formulation

| Component | w/w % |
|---|---|
| Terbinafine | 15 |
| Triacetin | 44 |
| SAIB | 37 |
| Ethanol | 4 |
| | 100 |

Other exemplary formulation according to embodiments of the invention are set forth in Table XXI, where the pharmaceutically active agent may be substituted with any active.

TABLE XXI

Formulations

| Identifier | Formula (w/w %) |
|---|---|
| 61 | 6% Lidocaine<br>30% SAIB with 10% Ethanol<br>64% Triacetin |
| 62 | 2% Tetracaine<br>30% SAIB with 10% Ethanol<br>68% Triacetin |
| 63 | 5% Lidocaine<br>2% Tetracaine<br>30% SAIB with 10% Ethanol<br>63% Triacetin |
| 64 | 7% Lidocaine<br>3% Tetracaine<br>30% SAIB with 10% Ethanol<br>60% Triacetin |
| 65 | 7% Lidocaine<br>41% SAIB with medium chain triglycerides<br>52% C8/C10 triglyceride |
| 66 | 7% Tetracaine<br>41% SAIB with medium chain triglycerides<br>52% C8/C10 triglyceride |
| 67 | 7% Lidocaine<br>40% SAIB with 10% Ethanol<br>15% Isopropyl myristate<br>19% Triacetin<br>19% C8/C10 triglyceride |
| 68 | 7% Lidocaine<br>41% SAIB with medium chain triglycerides<br>26% Triacetin<br>26% C8/C10 triglyceride |
| 69 | 7% Lidocaine<br>3% Tetracaine<br>41% SAIB with 20% C8/C10 triglyceride<br>24.5% Triacetin<br>24.5% C8/C10 triglyceride |
| 70 | 7% Lidocaine<br>41% SAIB with 20% C8/C10 triglyceride<br>35% Triacetin<br>17% C8/C10 triglyceride |

TABLE XXI-continued

Formulations

| Identifier | Formula (w/w %) |
|---|---|
| 71 | 7% Lidocaine<br>39% SAIB with 20% C8/C10 triglyceride<br>51% Triacetin<br>3% C8/C10 triglyceride |
| 72 | 7% Lidocaine<br>30% SAIB with 20% C8/C10 triglyceride<br>57% Triacetin<br>6% Propylene glycol<br>7% Lidocaine |
| 73 | 3% Tetracaine<br>30% SAIB with C8/C10 triglyceride<br>60% Triacetin |
| 74 | 7% Lidocaine<br>3% Tetracaine<br>70% SAIB<br>16% Triacetin<br>4% Ethanol |
| 75 | 7.75% Lidocaine<br>54% SAIB with 10% Ethanol<br>38.25% Triacetin |
| 76 | 7.5% Lidocaine<br>20% Glycerol monooleate<br>1% Tetracaine<br>10% Benzyl alcohol<br>5% Ethanol<br>56.5% C8/C10 triglyceride |
| 77 | 7.5% Lidocaine<br>20% Glycerol monooleate<br>10% Benzyl alcohol<br>5% Ethanol<br>57.5% C8/C10 triglyceride |
| 78 | 7.5% Lidocaine<br>25% Glycerol monooleate<br>10% Benzyl alcohol<br>5% Ethanol<br>49.5% C8/C10 triglyceride<br>3% Polyoxyl castor oil |

In some embodiments, the composition comprises a surfactant such as castor oil, hydrogenated castor oil, or polyoxyl castor oil such as KOLLIPHOR® ELP, KOLLIPHOR® HS15, KOLLIPHOR® RH40 or tocopherol polyethylene glycol succinate (TPGS), polysorbate (e.g., 20 and 80) or lecithin. In embodiments, the surfactant is present in an amount of about 0.01 to 10%, 0.05 to 10%, 0.5 to 5.0% or 1.5 to 4.5%. For example, in embodiments, the composition includes Polyoxyl castor oil in an amount of up to, or about 0.01, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0% w/w.

The formulation can also contain other inert ingredients such as antioxidants or preservatives. Antioxidants such as a propyl gallate, BHA (butylated hydroxy anisole), BHT (butylated hydroxy toluene), MTG (monothioglycerol), triethyl citrate, citric acid, TBHQ (tert-butyl hydroquinone) and the like may be added to the present formulation. The antioxidants are generally added to the formulation in amounts of from about 0.01 to about 2.0% (w/w). In certain embodiments, antioxidants are present in an amount of about 0.01 to 2.0%, 0.05 to 2.0%, 0.5 to 2.0% or 0.5 to 1.5%. For example, in embodiments, the composition includes MTG and/or citric acid in an amount of up to, or about 0.01, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0% w/w. In embodiments, the composition includes BHT and/or propyl galate in an amount of up to, or about 0.01, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0% w/w.

Preservatives such as the parabens (methylparaben and/or propylparaben) are suitably used in the formulation in amounts ranging from about 0.01 to about 2.0 w/w.

The formulation of the present invention may be prepared without addition of water to the mixture during any step of the process.

The disclosure provides pharmaceutical compositions comprising at least one pharmaceutically active agent in an amount effective for treating a disease or disorder, and a pharmaceutically acceptable vehicle. It is noted that the pharmaceutically active agent noted in any of the formulations herein may be substituted or augmented with a large variety of pharmaceutically active agents including, without limitation, antimicrobials, anti-inflammatories and analgesics. The pharmaceutically active agents may be hydrated; e.g., a monohydrate or dihydrate form of the molecule.

A suitable pharmaceutically active agent for use in the formulations described herein is an active pharmaceutical ingredient or a combination of a plurality of active ingredients. Such active pharmaceutical agents include, by way of illustration only, anthelmintics, analgesics, antiemetics, anti-inflammatories, steroids, sedatives, antimicrobials, stimulants, antidepressants, opioids, opiates, NSAIDS, cannabinoids, and anesthetics.

In embodiments, the active pharmaceutical agent is an antimicrobial agent, such as an anti-viral agent, antibiotic agent or antifungal agent.

As such, the disclosure provides compositions comprising at least one anti-viral agent, antimicrobial agent or antifungal agent in an amount effective for treating a disease or disorder, such as a microbial infection, and a pharmaceutically acceptable vehicle.

In some embodiments, an anti-viral agent for use in the formulations described herein is an integrase inhibitor. Examples of integrase inhibitors include cabotegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, and stilbenedisulfonic acid, T-169.

In some embodiments, an anti-viral agent for use in the formulations described herein is a nucleoside analogs, such as, but not limited to remdesivir, abacavir, acyclovir, adefovir, brivudine, cidofovir, clevudine, didanosine, edoxudine, emtricitabine, entecavir, famciclovir, floxuridine, ganciclovir, idoxuridine, inosine pranobex, lamivudine, penciclovir, sorivudine, stavudine, ribavirin, telbivudine, tenofovir, trifluridine, valacyclovir, valganciclovir, vidarabine, zalcitabine, and zidovudine. In certain embodiments, the antiviral agent is one that is effective in treating or preventing an infectious diseases such as those caused by Ebola virus, Zika virus, influenza or coronaviruses such as Coronavirus Disease 2019 (COVID-19), SARS associated coronavirus (SARS-CoV), or Middle East respiratory syndrome coronavirus (MERS-CoV).

In some embodiments, an antimicrobial agent for use in the formulations described herein is a fluoroquinolone antibiotic. Fluoroquinolones are compounds disclosed inter alia in the following documents: U.S. Pat. No. 4,670,444 (Bayer AG), U.S. Pat. No. 4,472,405 (Riker Labs), U.S. Pat. No.

4,730,000 (Abbott), U.S. Pat. No. 4,861,779 (Pfizer), U.S. Pat. No. 4,382,892 (Daiichi), U.S. Pat. No. 4,704,459 (Toyama), and specific examples which may be utilized are: benofloxacin, binfloxacin, cinoxacin, ciprofloxacin, danofloxacin, difloxacin, enoxacin, enrofloxacin, fleroxacin, ibafloxacin, levofloxacin, lomefloxacin, marbofloxacin, moxifloxacin, norfloxacin, ofloxacin, orbifloxacin, pefloxacin, pipemidic acid, temafloxacin, tosufloxacin, sarafloxacin, sparfloxacin.

In some embodiments, an antimicrobial agent for use in the formulations described herein is an amphenicol antibiotic. Ampenicol antibiotics may include, but are not limited to chloramphenicol, thiamphenicol, azidamfenicol and florfenicol.

In some embodiments, an antimicrobial agent for use in the formulations described herein is tetracycline, clindamycin or lincomycin.

In some embodiments, an antimicrobial agent for use in the formulations described herein is a macrolide antibiotic. Macrolide antibiotics may include, but are not limited to the mectins (including, without limitation, doximectin and abimectin), the mycins (including, without limitation, roxithromycin, clarithromycin, tulathromycin, gamithromycin, dirithromycin, fidaxomicin, megalomicin, erythromycin and the like), and azilides, such as azithromycin. The active agents are typically hydrated; e.g., a monohydrate or dehydrate form of the molecule.

In some embodiments, an antifungal agent for use in the formulations described herein is a triazole antifungal. Triazole antifungals may include, but are not limited to clotrimazole, ketoconazole, itraconazole, fluconazole, miconazole, econazole, butoconazole, oxiconazole, sulconazole, terconazole, posaconazole and voriconazole.

In some embodiments, an antifungal agent for use in the formulations described herein is a thiocarbamate antifungal. Thiocarbamate antifungals may include, but are not limited to tolnaftate.

In some embodiments, an antifungal agent for use in the formulations described herein is a polyene antifungal. Polyene antifungals may include, but are not limited to nystatin.

In one embodiment, an antifungal agent for use in the formulations described herein is terbinafine.

The disclosure provides compositions comprising at least one anti-inflammatory agent in an amount effective for treating a disease or disorder, such as pain or inflammation, and a pharmaceutically acceptable vehicle.

In some embodiments, an anti-inflammatory agent for use in the formulations described herein is an H1 or H2-blocker. Examples of H1-blockers include, but are not limited to clemastine and terfenadine. Examples of H2-blockers include, but are not limited to cimetidine, famotidine, nizatidine, and ranitidine.

In some embodiments, an anti-inflammatory agent for use in the formulations described herein is an NSAID. As used herein, the term "NSAID" refers to a class of therapeutic compounds with analgesic, anti-inflammatory, and anti-pyretic properties. NSAIDs reduce inflammation by blocking cyclooxygenase. NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclooxygenase (COX) inhibitor, a selective cyclooxygenase 1 (COX-1) inhibitor, and a selective cyclooxygenase 2 (COX-2) inhibitor. A NSAID may be a profen. Examples of a suitable salicylate derivative NSAID include, without limitation, Acetylsalicylic acid (aspirin), Diflunisal, Hydroxylethyl Salicylate, and Salsalate. Examples of a suitable p-amino phenol derivative NSAID include, without limitation, Paracetamol and Phenacetin. Examples of a suitable propionic acid derivative NSAID include, without limitation, Alminoprofen, Benoxaprofen, Dexketoprofen, Fenoprofen, Flurbiprofen, Ibuprofen, Indoprofen, Ketoprofen, Loxoprofen, Naproxen, Oxaprozin, Pranoprofen, And Suprofen. Examples of a suitable acetic acid derivative NSAID include, without limitation, Aceclofenac, Acemetacin, Actarit, Alcofenac, Aloxipirin, Amfenac, Aminophenazone, Antraphenine, Azapropazone, Benorilate, Benzydamine, Butibufen, Chlorthenoxacine, Choline Salicylate, Clometacin, Diclofenac, Emorfazone, Epirizole, Etodolac, Feclobuzone, Felbinac, Fenbufen, Fenclofenac, Glafenine, Indometacin, Ketorolac, Lactyl Phenetidin, Metamizole, Metiazinic Acid, Mofebutazone, Mofezolac, Nabumetone, Nifenazone, Niflumic Acid, Oxametacin, Pipebuzone, Propyphenazone, Proquazone, Protozininc Acid, Salicylamide, Sulindac, Tiaramide, Tinoridine, and Zomepirac. Examples of a suitable enolic acid (Oxicam) derivative NSAID include, without limitation, Droxicam, Isoxicam, Lornoxicam, Meloxicam, Piroxicam, and Tenoxicam. Examples of a suitable fenamic acid derivative NSAID include, without limitation, Flufenamic acid, Mefenamic acid, Meclofenamic acid, and Tolfenamic acid. Examples of a suitable selective COX-2 inhibitor include, without limitation, Celecoxib, Etoricoxib, Firocoxib, Lumiracoxib, Meloxicam, Parecoxib, Rofecoxib, and Valdecoxib.

A particular NSAID for use in the formulations described herein is a coxib. As used herein the term "coxib" refers to a selective cyclooxygenase-2 (COX-2) inhibitor or "COX-2 inhibitor".

In embodiments, the coxib may be any coxib known in the art, for example, and in no way limiting, mavacoxib, rofecoxib, celecoxib, cimicoxib, deracoxib, firocoxib, robenacoxib, valdecoxib, parecoxib, etoricoxib or any combination thereof.

In some embodiments, the coxib is mavacoxib, a non-steroidal anti-inflammatory drug (NSAID) of the coxib class (ATCvet Code QM01AH92). Mavacoxib-4-[5-(4-fluorophenyl)-3-(trifluoromethyl)-1H-pyrazol-1-yl]benzenesulfonamide is used in the treatment of chronic pain and inflammation associated with osteoarthritis in canines.

In some embodiments, the coxib is a "chromene coxib" and is a member of a structural class of COX-2 selective inhibitors of Formula (I):

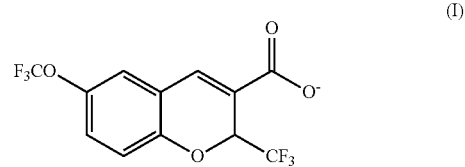 [SMILES: O=C([O-])C1=Cc2cc(OC(F)(F)F)ccc2OC1C(F)(F)F]

or an isomer or pharmaceutically acceptable salt thereof, or a compound of Formula (II):

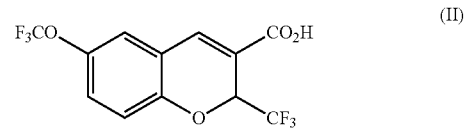 [SMILES: O=C(O)C1=Cc2cc(OC(F)(F)F)ccc2OC1C(F)(F)F]

or an isomer or pharmaceutically acceptable salt thereof.

Particular isomers or pharmaceutically acceptable salts of the compounds of Formulas (I) and (II) for use in compositions of the invention include Tris(hydroxymethyl)aminomethane (±)-6-(trifluoromethoxy)-2-(trifluoromethyl)-2H-chromene-3-carboxylate, (±)-6-(trifluoromethoxy)-2-(trifluoromethyl)-2H-chromene-3-carboxylic acid, Tris(hydroxymethyl)aminomethane (R)-6-(trifluoromethoxy)-2-(trifluoromethyl)-2H-chromene-3-carboxylate, (R)-6-(trifluoromethoxy)-2-(trifluoromethyl)-2H-chromene-3-carboxylic acid, Tris(hydroxymethyl)aminomethane (S)-6-(trifluoromethoxy)-2-(trifluoromethyl)-2H-chromene-3-carboxylate, and (S)-6-(trifluoromethoxy)-2-(trifluoromethyl)-2H-chromene-3-carboxylic acid.

The compositions of the present invention may include analgesic agents other than anti-inflammatory agents, such as opiates including buprenorphine, morphine, or local anesthetics such as, Lidocaine, Mepivacaine, Prilocaine, Procaine, Pentazocine, Benzocaine, Syntocaine, Tetracaine, Gingicaine, Articaine, Bupivacaine, Butanilicaine, Chloroprocaine, or, for example, Polidocanol.

Furthermore, the compositions may also include anti-inflammatory agents that could have a secondary effect as analgesics other than the analgesics listed above, which may in part have anti-inflammatory effects, such as corticosteroids or hormones, specifically Cortisone and corticoids, such as glucocorticoids (e.g., Cortisone, Cloprednol, Prednisone, Prednisolone, Methylprednisolone, Deflazacort, Fluocortolone, Triamcinolone, Dexamethasone, Betamethasone) and mineral corticoids (e.g., Aldosterone, Desoxycorticosterone, Fludrocortisone).

In an embodiment, the composition includes a corticosteroid selected from amcinonide, betamethasone benzoate, betamethasone dipropionate, betamethasone valerate, clobetasol propionate, clocortolone pivalate, desonide, desoximetasone, dexamethasone, dexamethasone sodium phosphate, diflorasone diacetate, fluocinonide, fluocinolone acetonide, flurandrenolide, fluticasone propionate, halcinonide, halobetasol propionate, hydrocortisone, hydrocortisone butyrate, hydrocortisone valerate, mometasone furoate, prednisolone acetate, triamcinolone acetonide, and the combination thereof.

The pharmaceutically active compounds of the disclosure may also be formulated into compositions as natural or salt forms. Pharmaceutically acceptable non-toxic salts include the base addition salts (formed with free carboxyl or other anionic groups), which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure include amine salts formed by the protonation of an amino group with inorganic acids such as hydrochloric acid, hydrobromic acid, hydroiodic acid, sulfuric acid, phosphoric acid, and the like. Salts of the disclosure may also include amine salts formed by the protonation of an amino group with suitable organic acids, such as p-toluenesulfonic acid, acetic acid, and the like.

Additional excipients which are contemplated for use in the practice of the disclosure are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the compounds are included in the disclosure. It should be noted that while the hydrate molecules will contribute water to the pharmaceutical composition, it is envisioned that no other water source be included.

The composition may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a carrier suitable for administration via an intended route, specifically, injection. In the pharmaceutical composition, the active compound is included in an amount sufficient to produce the desired effect upon the process or condition of diseases.

For the compositions of the invention, the pharmaceutically active agent need only be administered by single subcutaneous injection (allowing use of higher doses), one time for an entire course of treatment to clinically resolve a disease or disorder. However, the pharmaceutically active agent may be administered by a series of subcutaneous injection, such as 1, 2, 3, 4, 5, 6, 7, 8, 9, 10 or more injections as necessary over a duration to clinically resolve a disease or disorder. In respects, "clinically resolve" may be measured by reference to the clinically significant and measurable presence of the active in the animal's bloodstream (at least about 1.0 ng/ml) for the requisite period of time; e.g., at least about 48, 60, 72, 84, 96, 108, 120, 132, 144, 156, 168 hours or greater. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition.

Similarly, it is anticipated that the formulations of the disclosure achieve at least 75, 80, 85, 90, 91, 92, 93, 94, 95, 96, 97, 98, 99 or 100% cure rate of the disease or disorder upon single injection. It is expected that patients administered the formulations will show at least 75, 80, 85, 90, 91, 92, 93, 94, 95, 96, 97, 98, 99 or 100% cure within 1, 2, 3, 4, 5, 6, 7, 8, 9, 10, 11, 12, 13, 14, 15, 16, 17, 18, 19, 20 or 21 days of administration.

As used herein, "cure rate" refers to clinical efficacy at resolving the disease or disorder, such as infection, pain or inflammation. In embodiments, the disease or disorder is resolved with an efficacy greater than about 75, 80, 85, 90, 91, 92, 93, 94, 95, 96, 97, 98, 99 or up to 100%, within a duration of less than 1, 2, 3, 4, 5, 6, 7, 8, 9, 10, 11, 12, 13, 14, 15, 16, 17, 18, 19, 20 or 21 days after a single administration.

In embodiments, an appropriate active concentration level will generally be about 0.01 to about 500.0 mg/ml or about 0.1 to about 250.0 mg/ml, such as, for example, about 0.25 to 500.0 mg/ml, 1.0 to 400.0 mg/ml, 5.0 to 250.0 mg/ml, 1.0 to 100.0 mg/ml, 5.0 to 150.0 mg/ml, 10.0 to 250.0 mg/ml, 10.0 to 200.0 mg/ml, 15.0 to 250.0 mg/ml or 15.0 to 200.0 mg/ml (including all intermediate dosages) all in a single injection form.

In embodiments, an appropriate active concentration level will generally be about 0.1 to about 30.0 mg/ml or about 0.1 to about 25.0 mg/ml, such as, for example, about 0.25 to 30.0 mg/ml, 1.0 to 25.0 mg/ml, 5.0 to 25.0 mg/ml, 1.0 to 10.0 mg/ml, 5.0 to 15.0 mg/ml, 10.0 to 25.0 mg/ml, 10.0 to 20.0 mg/ml, 15.0 to 25.0 mg/ml or 15.0 to 20.0 mg/ml (including all intermediate dosages) all in a single injection form.

In embodiments, upon administration of the composition of the invention to a subject, at least about 10, 50, 100, 500, 1,000, 2,000, 3,000, 4,000, 5,000, 10,000, 15,000, 20,000, 25,000, 30,000, 35,000, 40,000, 45,000 or 50,000 ng/ml of the pharmaceutically active agent is present in the blood stream of the subject for at least about 48, 60, 72, 84, 96, 108, 120, 132, 144, 156, 168 hours or greater upon administration to a mammal. In various embodiments, upon administration of the composition of the invention to a subject, at least about 10, 50, 100, 500, 1,000, 2,000, 3,000, 4,000, 5,000, 10,000, 15,000, 20,000, 25,000, 30,000, 35,000, 40,000, 45,000 or 50,000 ng/ml of the pharmaceutically active agent is present in the blood stream of the subject for at least about 48, 60, 72, 84, 96, 108, 120, 132, 144, 156, 168 hours or greater upon a single administration to a mammalian subject.

The formulations of the invention are particularly useful in mammals, especially companion animals, and most especially cats and dogs.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Example I

Formulations

The following marbofloxacin containing formulations were prepared for subcutaneous injection to canines to treat urinary tract infection (UTI).

TABLE XXII

| Formulations Marbofloxacin Injection for Dogs | |
|---|---|
| Identifier | Formula (% w/w) |
| 22 | 5% Dehydrated Ethanol |
|  | 5% Benzyl Alcohol |
|  | 50% Medium chain triglycerides (e.g., caprickaprylic triglycerides) |
|  | 20% glycerol monooleate |
|  | 20% Marbofloxacin |
| 23 | 20% Marbofloxacin |
|  | 20% Glycerol monooleate |
|  | 3% Polyoxyl castor oil |
|  | 5% Hydrogenated phosphatidylcholine from soybean lecithin |
|  | 10% Benzyl Alcohol |
|  | 5% Dehydrated Ethanol |
|  | 0.07% Vitamin E |
|  | 36.93% Medium chain triglycerides (e.g., capric/caprylic triglycerides) |

EXAMPLE II

Pharmacokinetics of a Formulation of the Invention

Dogs were dosed by subcutaneous injection with a formulation of Table XXII (Formulation 22) at a dosing concentration of about 20 mg/kg. Blood concentrations of marbofloxacin were present at clinically significant levels (above about 1 ng/ml) for more than 160 hours following administration of the composition, as shown in FIG. 1 (dotted line).

Example III

Pharmacokinetics of a Formulation of the Invention

Dogs were dosed by subcutaneous injection with the formulation of Table XXII (Formulation 23) at a dosing concentration of about 20 mg/kg. Blood concentrations of marbofloxacin were present at clinically significant levels (above about 1 ng/ml) for more than 160 hours following administration of the composition, as shown in FIG. 1 (solid line).

Example IV

Formulations

The following florfenicol containing formulations were prepared.

TABLE XXIII

| Formulations Florfenicol Injection for Dogs | |
|---|---|
| Identifier | Formula (w/w %) |
| 59 | 15% Florfenicol |
|  | 4% Ethanol, dehydrated |
|  | 44% Triacetin |
|  | 37% SAIB |
| 60 | 20% Florfenicol |
|  | 20% Glycerol monooleate |
|  | 5% Benzyl alcohol |
|  | 47% C8/C10 triglyceride |
|  | 3% Polyoxyl castor oil |
|  | 5% Ethanol, dehydrated |

Example V

In Virto Kinetics of a Formulation of the Invention

In vitro release rates were analyzed for the formulations of Table XXIII.

The formulations were compounded. Vessel were filled with 600 mL of phosphate buffer and allowed to equilibrate. Using a 1-mL syringe equipped with a 6-inch stainless steel needle, each vessel was inoculated with 1.0 mL of the formulation, forming a depot. Approximately 2 mL of the media from each vessel was retrieved at time intervals (T0 (3 h), T1 (24 h), T2 (48 h), T3 (72 h), T5 (120 h), and infinity) and measured for UV absorbance in a spectrophotometer to determine the percent of active released from the depot.

Figure 2:
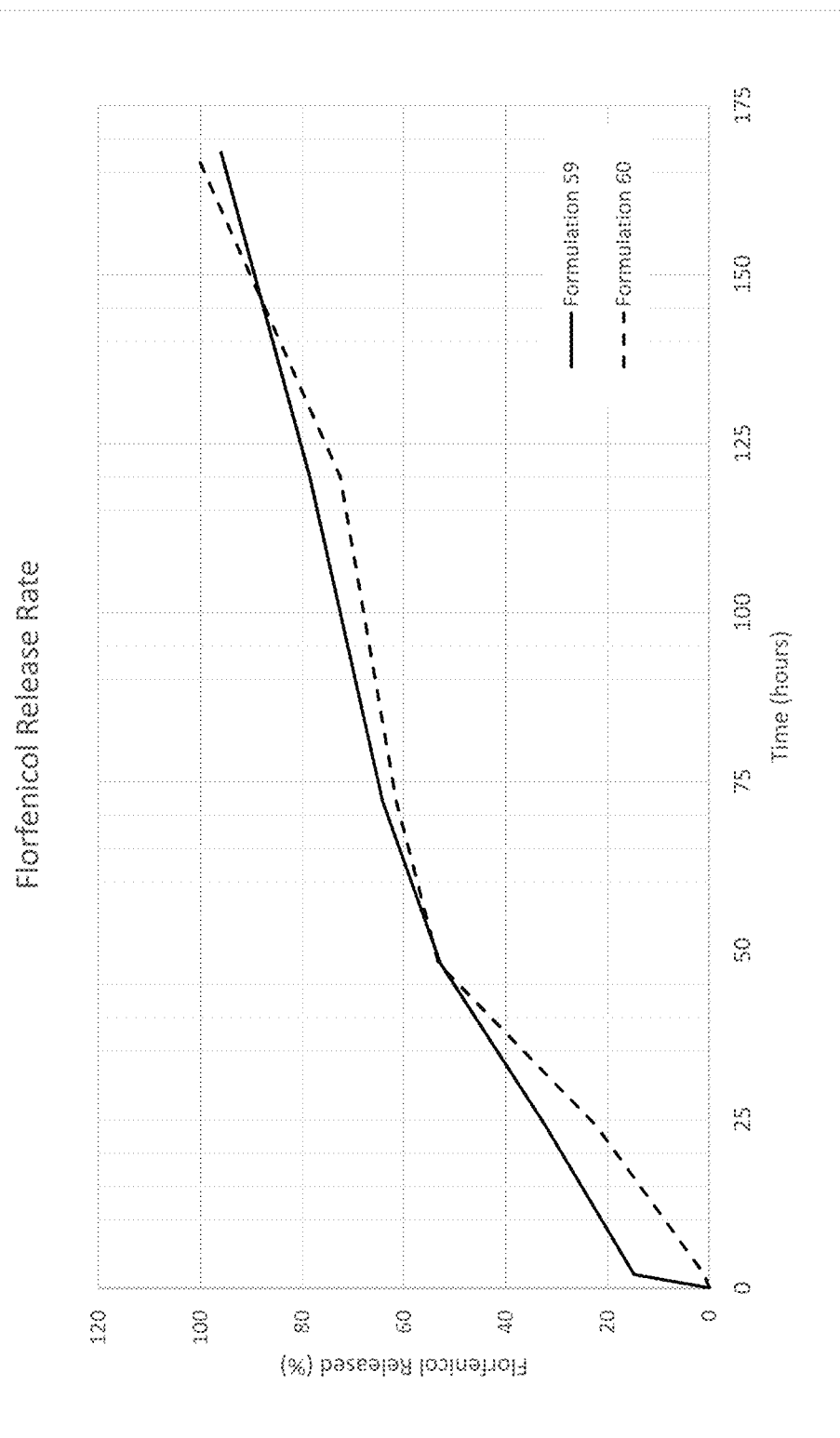
FIG. 2 is a graphical representation depicting data in one embodiment of the invention.

The results are shown in FIG. 2. 100% release was evidenced at greater than 150 for both Formulations 59 and 60.

Example VI

Pharmacokinetics of a Formulation of the Invention

Figure 3:
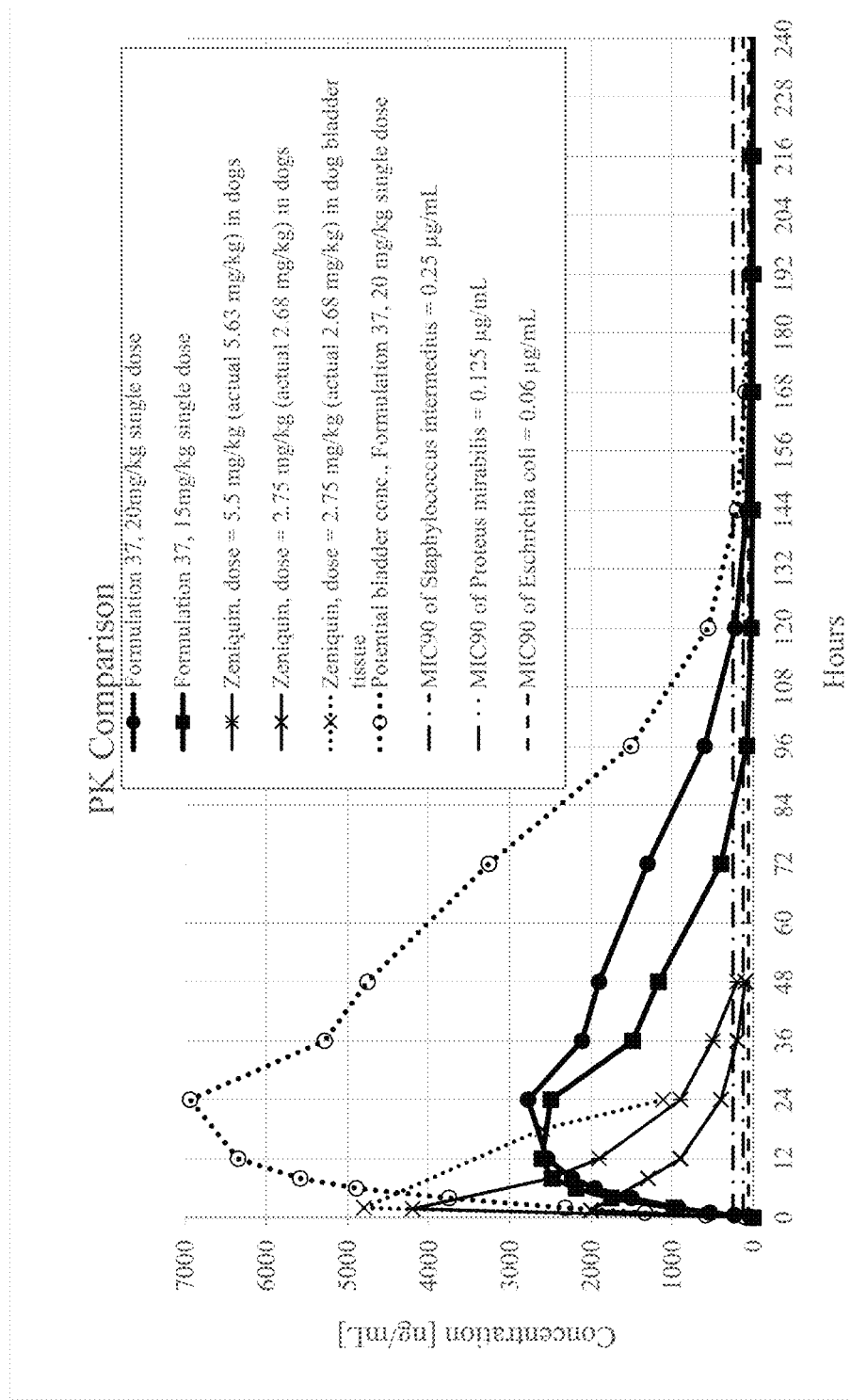
FIG. 3 is a graphical representation depicting data in one embodiment of the invention.

Formulation 37 from Table VIII containing marbofloxacin was prepared for subcutaneous injection to canines to treat UTI. Dogs were dosed by subcutaneous injection with Formulation 37 at a dosing concentration of about 15 mg/kg and about 20 mg/kg. FIG. 3 shows PK curves with comparison to Zeniquin®. Potential bladder concentration of marbofloxacin was determined for Formulation 37 administered at a dosing concentration of about 20 mg/kg showing higher amounts of marbofloxacin being released to the bladder for a longer duration as compared with Zeniquin®.

Example VII

Pharmacokinetics of a Formulation of the Invention

Figure 4:
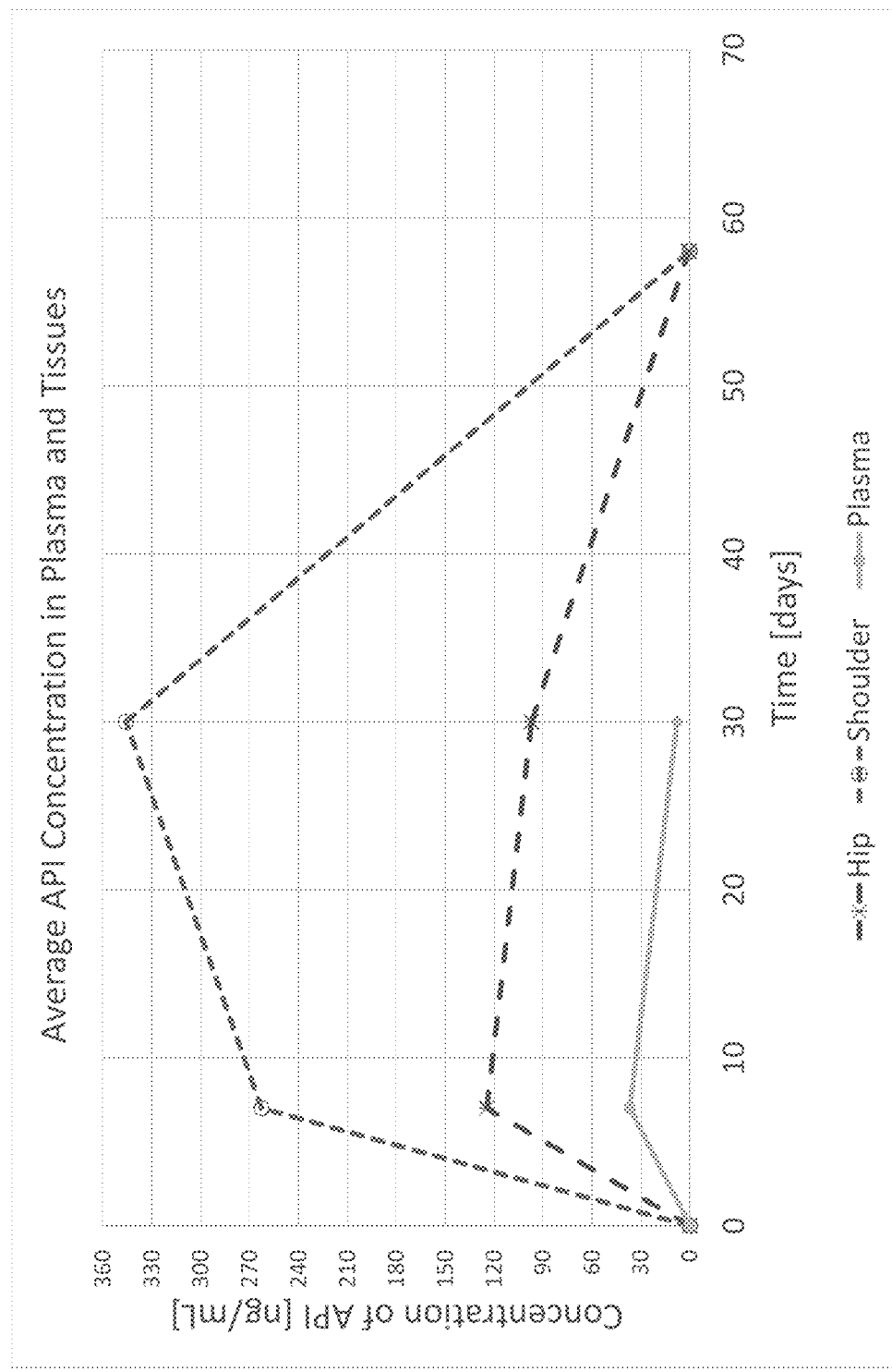
FIG. 4 is graphical representation depicting data in one embodiment of the invention.

The formulation of Table XX containing terbinafine was prepared for subcutaneous injection to canines. Dogs were dosed by subcutaneous injection with the formulation at a dosing concentration of about 30 mg/kg. FIG. 4 shows the concentration of terbinafine in plasma and tissue (via skin punch analysis) upon administration.

Although the objects of the disclosure have been described with reference to the above example, it will be understood that modifications and variations are encompassed within the spirit and scope of the disclosure. Accordingly, the disclosure is limited only by the following claims.

What is claimed is:

1. A non-aqueous, extended release, injectable pharmaceutically acceptable composition, comprising:
   a) a pharmaceutically active agent present at about 1.0 to 25% w/w;
   b) glycerol monooleate present at about 5.0 to 40.0% w/w;
   c) a C8 triglyceride, a C10 triglyceride, or a combination thereof present at about 5.0 to 80.0% w/w;
   d) ethanol and benzyl alcohol present at about 1 to 25% w/w in combination; and
   e) a surfactant present in an amount of about 0.5 to 5.0% w/w,
   wherein the composition forms a water-insoluble depot upon injection wherein the pharmaceutically acceptable active agent is selected from a fluroquinolone and florfenicol, and wherein upon subcutaneous injection, at least 90% of the pharmaceutically active agent is released by about 150 hours.

2. The composition of claim 1, comprising:
   the glycerol monooleate present at about 20% w/w;
   C8 triglyceride, a C10 triglyceride, or a combination thereof present at about 60% w/w; and
   the ethanol and benzyl alcohol present at about 10% w/w in combination.

3. The composition of claim 1, wherein the fluoroquinolone is benofloxacin, binfloxacin, cinoxacin, ciprofloxacin, danofloxacin, difloxacin, enoxacin, enrofloxacin, fleroxacin, ibafloxacin, levofloxacin, lomefloxacin, marbofloxacin, moxifloxacin, norfloxacin, ofloxacin, orbifloxacin, pefloxacin, pipemidic acid, temafloxacin, tosufloxacin, sarafloxacin, sparfloxacin, or combination thereof.

4. The composition of claim 1, further comprising an excipient.

5. The composition of claim 1, further comprising polyoxyl castor oil.

6. The composition of claim 1, further comprising hydrogenated phosphatidylcholine from soybean lecithin.

7. The composition of claim 1, further comprising an anti-oxidant.

8. The composition of claim 1, further comprising cholesterol.

9. The composition of claim 1, wherein the C8 triglyceride is caprylic acid, and the C10 triglyceride is capric acid.

10. The composition of claim 1, wherein at least about 100, 500, 1,000, 2,000, 3,000, 4,000, 5,000, 10,000, 15,000 or 20,000 ng/ml of the pharmaceutically active agent is present in the blood stream of a subject for at least about 48, 60, 72, 84, 96, 108, 120, 132, 144, 156, 168 hours or greater upon administration to a mammal.

11. A method of treating a disease or disorder in a subject, comprising administering to the subject an effective amount of the composition of claim 1.

12. The method of claim 11, wherein the subject is a mammal.

13. The method of claim 12, wherein the subject is a canine.

14. The method of claim 11, wherein the subject is a feline.

15. The method of claim 11, wherein the disease or disorder is an infection.

16. The method of claim 11, wherein at least about 100, 500, 1,000, 2,000, 3,000, 4,000, 5,000, 10,000, 15,000 or 20,000 ng/ml of the pharmaceutically active agent is present in the blood stream of the subject for at least about 48, 60, 72, 84, 96, 108, 120, 132, 144, 156, 168 hours or greater upon administration to a mammal.

17. An extended release, injectable pharmaceutically acceptable composition comprising:
   a) a pharmaceutically active agent that is marbofloxacin present at about 15 to 25% w/w;
   b) glycerol monooleate present at about 15 to 40% w/w;
   c) a C8 triglyceride, a C10 triglyceride, or a combination thereof present at about 40 to 55% w/w;
   d) ethanol present at about 1 to 10% w/w; and
   e) benzyl alcohol present at about 1 to 10% w/w;
   wherein the composition forms a water-insoluble depot upon injection,
   wherein the composition is suitable for either subcutaneous or intramuscular injection and wherein upon subcutaneous injection, at least 90% of the pharmaceutically active agent is released by about 150 hours.

* * * * *